(12) United States Patent
Distefano et al.

(10) Patent No.: US 10,940,666 B2
(45) Date of Patent: Mar. 9, 2021

(54) PACKAGING STRUCTURES AND ADDITIVE MANUFACTURING THEREOF

(71) Applicant: Howmedica Osteonics Corp., Mahwah, NJ (US)

(72) Inventors: Nicole Distefano, Denville, NJ (US); Marc Esformes, Wappingers Falls, NY (US); Robert W. Klein, Orangeburg, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 79 days.

(21) Appl. No.: 15/988,355

(22) Filed: May 24, 2018

(65) Prior Publication Data

US 2018/0339486 A1    Nov. 29, 2018

Related U.S. Application Data

(60) Provisional application No. 62/511,539, filed on May 26, 2017.

(51) Int. Cl.
| | |
|---|---|
| *B65D 81/02* | (2006.01) |
| *B65D 81/05* | (2006.01) |
| *B29C 64/118* | (2017.01) |
| *B32B 3/26* | (2006.01) |
| *B32B 27/08* | (2006.01) |
| *B32B 27/34* | (2006.01) |
| *B33Y 30/00* | (2015.01) |

(Continued)

(52) U.S. Cl.
CPC .............. *B32B 3/26* (2013.01); *B29C 64/118* (2017.08); *B32B 27/08* (2013.01); *B32B 27/34* (2013.01); *B65D 81/022* (2013.01); *B65D 81/05* (2013.01); *A61F 2/0095* (2013.01); *B29L 2031/712* (2013.01); *B32B 2250/03* (2013.01); *B32B 2305/026* (2013.01); *B32B 2439/80* (2013.01); *B33Y 30/00* (2014.12); *B33Y 80/00* (2014.12)

(58) Field of Classification Search
CPC .. B65D 81/022; B65D 81/113; B65D 81/133; B65D 81/3823; B65D 85/34; B65D 83/0436; B65D 47/2025; B65D 77/0446; B32B 3/26; B32B 3/30; B32B 2250/03; B32B 2305/024; B32B 2305/026; B32B 2305/02; B32B 2439/08
USPC ........................................................ 206/524
See application file for complete search history.

(56) References Cited

U.S. PATENT DOCUMENTS

| | | |
|---|---|---|
| 4,309,778 A | 1/1982 | Buechel et al. |
| 5,413,116 A | 5/1995 | Radke et al. |

(Continued)

FOREIGN PATENT DOCUMENTS

| | | |
|---|---|---|
| EP | 1738720 A2 | 1/2007 |
| FR | 2682287 A1 | 4/1993 |

(Continued)

*Primary Examiner* — Mollie Impink
(74) *Attorney, Agent, or Firm* — Lerner, David, Littenberg, Krumholz & Mentlik, LLP (57) ABSTRACT

A packaging system includes a packaging unit and an article. The packaging unit includes a solid layer, a porous layer and a plastic layer with a cavity. The cavity is configured to receive and secure the article in an opening defined by the cavity that is flexible between a first and a second dimension. The packaging unit is fabricated by a 3D printing process. A tensioning device of a 3D printing machine tensions a feed filament during the 3D printing process.

10 Claims, 8 Drawing Sheets

(51) Int. Cl.
*B33Y 80/00* (2015.01)
*B29L 31/00* (2006.01)
*A61F 2/00* (2006.01)

(56) References Cited

U.S. PATENT DOCUMENTS

| | | | |
|---|---|---|---|
| 5,533,519 | A | 7/1996 | Radke et al. |
| 5,593,450 | A | 1/1997 | Scott et al. |
| 5,709,460 | A | 1/1998 | Lester |
| 7,387,644 | B2 | 6/2008 | Beynnon et al. |
| 7,806,898 | B2 | 10/2010 | Justin et al. |
| 8,002,839 | B2 | 8/2011 | Rochetin et al. |
| 8,142,509 | B2 | 3/2012 | McKinnon et al. |
| 8,236,060 | B2 | 8/2012 | Justin et al. |
| 8,236,061 | B2 | 8/2012 | Heldreth et al. |
| 8,282,685 | B2 | 10/2012 | Rochetin et al. |
| 8,475,535 | B2 | 7/2013 | Otto |
| 8,480,754 | B2 | 7/2013 | Bojarski et al. |
| 8,506,639 | B2 | 8/2013 | Hayden et al. |
| 8,556,983 | B2 | 10/2013 | Bojarski et al. |
| 8,652,210 | B2 | 2/2014 | Otto et al. |
| 8,728,387 | B2 | 5/2014 | Jones et al. |
| 8,771,365 | B2 | 7/2014 | Bojarski et al. |
| 8,777,875 | B2 | 7/2014 | Park |
| 8,911,502 | B2 | 12/2014 | Li et al. |
| 8,926,706 | B2 | 1/2015 | Bojarski et al. |
| 8,974,539 | B2 | 3/2015 | Bojarski et al. |
| 9,020,788 | B2 | 4/2015 | Lang et al. |
| 9,180,010 | B2 | 11/2015 | Dong et al. |
| 9,320,616 | B2 | 4/2016 | Samuelson et al. |
| 9,320,620 | B2 | 4/2016 | Bojarski et al. |
| 9,358,117 | B2 | 6/2016 | Collazo et al. |
| 9,387,079 | B2 | 7/2016 | Bojarski et al. |
| 9,402,729 | B2 | 8/2016 | Otto et al. |
| 2003/0158606 | A1 | 8/2003 | Coon et al. |
| 2005/0143833 | A1 | 6/2005 | Merchant |
| 2006/0142657 | A1 | 6/2006 | Quaid et al. |
| 2006/0190086 | A1 | 8/2006 | Clemow et al. |
| 2008/0058945 | A1 | 3/2008 | Hajaj et al. |
| 2009/0222103 | A1 | 9/2009 | Fitz et al. |
| 2011/0087332 | A1 | 4/2011 | Bojarski et al. |
| 2011/0144760 | A1 | 6/2011 | Wong et al. |
| 2011/0218635 | A1 | 9/2011 | Amis et al. |
| 2012/0172993 | A1 | 7/2012 | Wright et al. |
| 2012/0191205 | A1 | 7/2012 | Bojarski et al. |
| 2012/0191420 | A1 | 7/2012 | Bojarski et al. |
| 2013/0204252 | A1 | 8/2013 | Samuelson et al. |
| 2013/0211531 | A1 | 8/2013 | Steines et al. |
| 2013/0289729 | A1 | 10/2013 | Bonutti |
| 2014/0005997 | A1 | 1/2014 | Park et al. |
| 2014/0039631 | A1 | 2/2014 | Bojarski et al. |
| 2014/0052611 | A1* | 2/2014 | Cutsforth ............. B65D 81/058 705/39 |
| 2014/0138014 | A1* | 5/2014 | Chaudhry ................. B32B 5/18 156/77 |
| 2014/0142713 | A1 | 5/2014 | Wright et al. |
| 2014/0142714 | A1 | 5/2014 | Wright et al. |
| 2014/0228964 | A1 | 8/2014 | Lew et al. |
| 2014/0358241 | A1 | 12/2014 | Afriat |
| 2014/0378978 | A1 | 12/2014 | Park |
| 2015/0196325 | A1 | 7/2015 | Shenoy et al. |
| 2015/0258735 | A1 | 9/2015 | O'Neill et al. |
| 2015/0297353 | A1 | 10/2015 | Amis et al. |
| 2015/0342739 | A1 | 12/2015 | Mahfouz |
| 2015/0374386 | A1 | 12/2015 | Collazo et al. |
| 2016/0009029 | A1 | 1/2016 | Cohen et al. |
| 2016/0143744 | A1 | 5/2016 | Bojarski et al. |
| 2016/0217268 | A1 | 7/2016 | Otto et al. |
| 2016/0228197 | A1 | 8/2016 | Park et al. |
| 2016/0228255 | A1 | 8/2016 | Samuelson et al. |
| 2016/0235420 | A1 | 8/2016 | Collazo et al. |

FOREIGN PATENT DOCUMENTS

| | | | |
|---|---|---|---|
| FR | 2845669 A1 * | 4/2004 | ........... B65D 81/113 |
| WO | 0170143 A1 | 9/2001 | |
| WO | 2007013959 A2 | 2/2007 | |
| WO | 2014131007 A1 | 8/2014 | |

* cited by examiner

PACKAGING STRUCTURES AND ADDITIVE MANUFACTURING THEREOF

CROSS-REFERENCE TO RELATED APPLICATION

The present application claims the benefit of the filing date of U.S. Provisional patent application No. 62/511,539, filed on May 26, 2017, the disclosure of which is hereby incorporated by reference.

FIELD OF INVENTION

The present invention relates generally to a packaging structure and the fabrication of such a structure, and in particular relates to a multi-layered packaging structure and a process for fabricating the packaging structure by additive layer manufacturing.

BACKGROUND OF THE INVENTION

Medical devices must be packaged for safe storage, shipping and handling. Packaging structures also often need to provide a sterile environment for medical devices. Conventional packaging for such medical devices includes an exterior rigid layer to resist puncture and abrasion, a flexible porous layer to provide shock absorption, and a sterile layer to prevent contamination during storage, shipping and handling of these articles. In many such packaging structures, the rigid layer is fabricated from polyethylene terephthalate glycol-modified ("PETG"), and the shock-absorbing flexible layer is fabricated from thermoplastic polyurethane ("TPU") and provided with a sterile barrier. The sterile barrier is often DuPont TYVEK® that is applied using heat and pressure after inserting the medical device into a packaging structure.

Such multi-purpose packaging structures are often fabricated from a plurality of different materials using a conventional technique such as injection molding, machining, thermoforming, extrusion, die cutting or blow molding that do not allow for intricate packaging features and designs without additional processing. For example, undercuts, snap fit features, or other intricate features such as clasps cannot be fabricated with sufficient definition to closely conform to the dimensions of an article being shipped or otherwise operate to retain the article. For example, medical-grade TPU is generally available in extruded sheets, which are then heat formed and assembled into a multi-layered packaging structure. An open mold is generally used in such thermoforming processes, wherein only one surface of the heat formed sheet is in contact with the mold. The second surface of the sheet is only indirectly defined by the mold and thus lacks precise definition.

Furthermore, complex features such as open cells, struts, and walls, for controlling hardness and plasticity for rigidity and shock absorbance require custom fabrication of individual portions or sections of packaging structures which must then be assembled, adding significant cost. Packaging structures assembled from different materials also require multiple raw materials to be ordered, stocked, and handled.

Additive manufacturing enables the formation of a continuous structure using a single feed material to form a packaging unit with multiple layers of varying hardness and elasticity. However, certain sterile materials preferred for medical devices, such as medical-grade TPU, have a higher elasticity than other plastics such as standard TPU and are therefore generally incompatible with 3D printing. Using such materials in additive manufacturing processes such as 3D printing can result in slack within a feed filament that can jam a printing head of a 3D printing machine.

Therefore, there exists a need for a multi-functional packaging system for use with highly elastic materials.

SUMMARY OF THE INVENTION

In accordance with one aspect of the invention, a multi-layered packaging structure for retaining an article, such as a medical device, may include an outer solid layer and an inner plastic layer which may be separated by a porous intermediate layer. Each of these layers may be configured to provide specific attributes to allow for storage, handling and shipping of the article. The inner plastic layer may include a cavity sized to securely retain the article. In accordance with another aspect of the invention, such packaging structures may be formed by an additive manufacturing process. For example, three-dimensional (3D) printing with a single feed material, such as medical-grade TPU, may be applied in successive layers to form sterile packaging structures to retain articles, such as medical devices, required to maintain sterility. In accordance with another aspect of the invention, a tensioning device may be coupled to a 3D printer assembly to provide adjustable feed filament tension. In this manner, highly elastic materials such as medical-grade TPU may be 3D printed into a packaging structure. A packaging system may include such a packaging structure and a sterilized article retained by the packaging structure which maintains the integrity and sterility of the article during storage, shipping and handling.

In accordance with another aspect of the invention, a multi-layered packaging structure for retaining an article, such as a medical device, may include a substantially solid first layer, a porous second layer, and a plastic third layer. Each of these layers may be configured to provide specific attributes to allow for sterilization, storage, handling, shipping, and removal of the article by the user in a sterile environment. The plastic third layer may define a cavity with an opening that may be flexible between a first and a second dimension, the second dimension may be greater than the first dimension. The second layer may be disposed between the first and the third layers. In some arrangements, the cavity may also have a third dimension which is greater than the first dimension.

In accordance with another aspect, a multi-layered packaging structure may include a substantially solid first layer, a porous second layer, and a plastic third layer. The second layer may be disposed between the first and the third layers and may define a cavity with an opening having a first dimension. An article may have a second dimension that is substantially the same or greater than the first dimension. The article may be received and secured within the cavity and may be removable from the cavity.

In some arrangements, the article may be a medical implant.

In some arrangements, the packaging structure may include a cover that may enclose the opening in a first position and may expose the opening in a second position. The cover may enclose the cavity in the first position. In some arrangements, the cover may be hingedly attached to the first layer and may be inseparable from the first layer without fracturing either of the cover and the first layer.

In some arrangements, the packaging structure may be a monolithic structure and may be made from an elastomeric material.

In accordance with another aspect, an article may be packaged. In packaging the article, a packaging unit with an inner wall defining a cavity may be printed by an additive manufacturing process. The article may be inserted into the cavity of the packaging unit such that the inner wall at least partially surrounds the article to secure the article.

In some arrangements, the article may be a medical implant. In some arrangements, the article may be enclosed within the packaging unit such that the article is removable from the packaging unit.

In some arrangements, the packing unit may be printed by an elastomeric film. In some arrangements, the printed packaging unit may be a monolithic structure.

In some arrangements, a cover may be placed on the packaging unit and over the inserted article. In some arrangements, the cavity may be sealed by heating or utilizing a chemical polymerization process to fuse the packaging unit and the cover to form a sterilized barrier for the inserted article.

In accordance with another aspect, a 3D printing assembly for use in printing elastomeric material may include a frame structure, a build platform, a tensioning device and a printing head. The build platform may be attached to the frame structure. The tensioning device may be attached to the frame structure to contact and apply tension to a feed filament. The printing head may be attached to the frame structure to dispense the tensioned feed filament as an elastomeric material onto the build platform. In this manner, highly elastic materials such as medical-grade TPU may be 3D printed into a packaging unit.

In some arrangements, the tensioning device may include a housing and a band. The housing may include a filament inlet and a filament outlet to receive the feed filament. The band may be disposed around the housing. An inner side of the band may have a projection that may engage with the housing in a first position and that may disengage from the housing in a second position. The engagement of the projection and the housing in the first position may press at least a portion of the housing against the feed filament when the feed filament is received in the housing. In this manner, the tension may be applied to the feed filament. In some arrangements, the size of the filament inlet may be variable to adjust the tension applied to the feed filament.

In some arrangements, the housing may define a groove. The band may be rotatable relative to the housing such that the projection may progressively engage with the groove when the band is engaged with the housing to adjust the tension applied to the feed filament.

BRIEF DESCRIPTION OF THE DRAWINGS

A more complete appreciation of the subject matter of the present invention and the various advantages thereof may be realized by reference to the following detailed description, in which reference is made to the following accompanying drawings.

DETAILED DESCRIPTION

Figure 1:
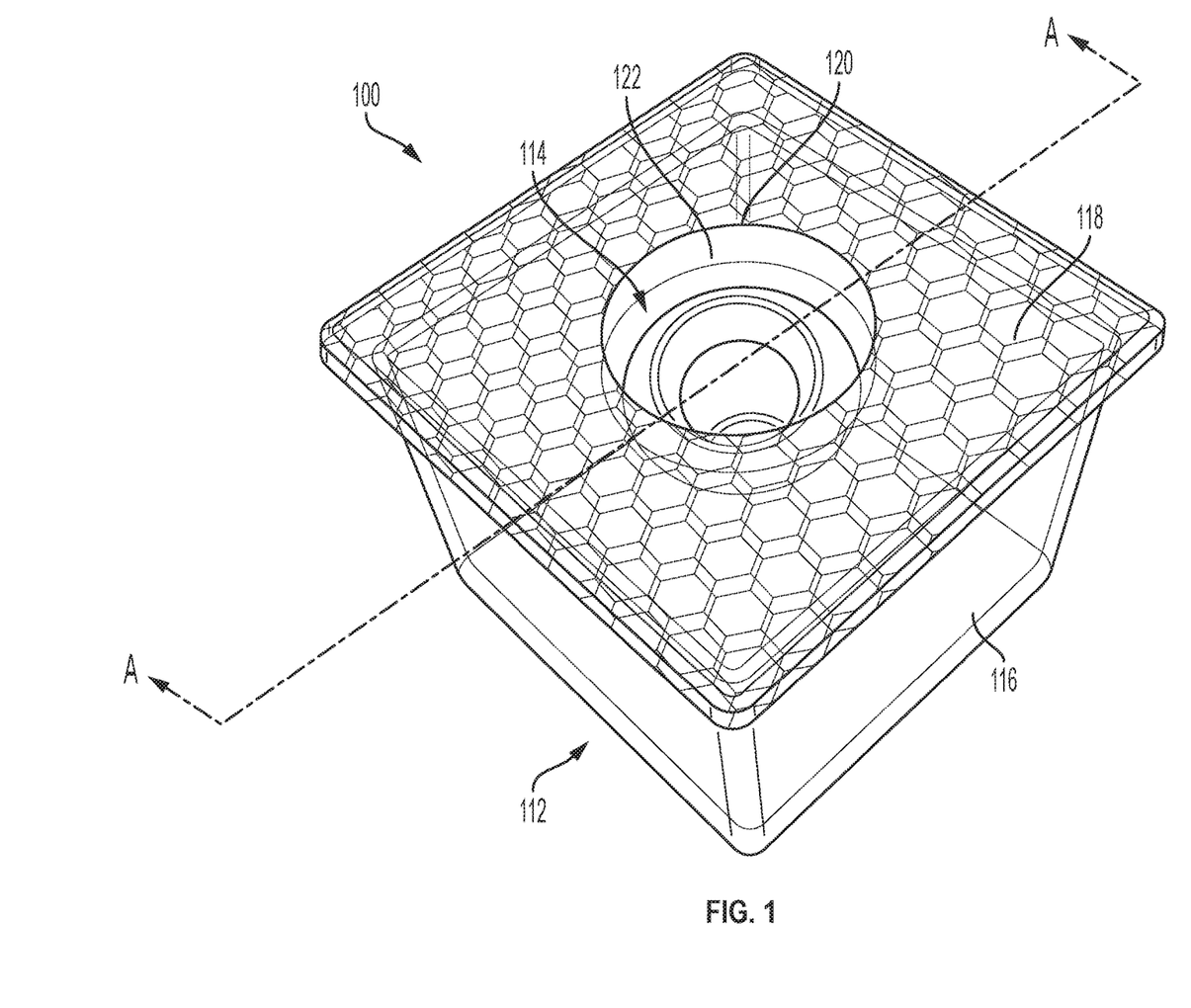
FIG. 1 is a perspective view of a packaging system in accordance with an embodiment.

Referring now to the drawings, as shown in FIG. 1, packaging system 100 includes packaging unit 112 and article 114. Packaging unit 112 includes solid exterior layer 116, intermediate porous layer 118, and inner layer 120 defining cavity 122. Packaging unit 112 may be an integral, i.e., monolithic, structure, such that exterior layer 116, porous layer 118, and inner layer 120 are inseparable from each other without fracture of any one of these layers. In the example shown, packaging unit 112 is in the form of a cube, although the packaging unit may be in other forms that retains article 114. Packaging unit 112 may be but is not limited to being made of materials such as plastics, which may be but are not limited to being polyamides, alumides, acrylonitrile butadiene styrene ("ABS"), TPU, medical-grade TPU, etc. In the preferred arrangement shown, packaging unit 112 is made of medical-grade TPU.

Figure 2:
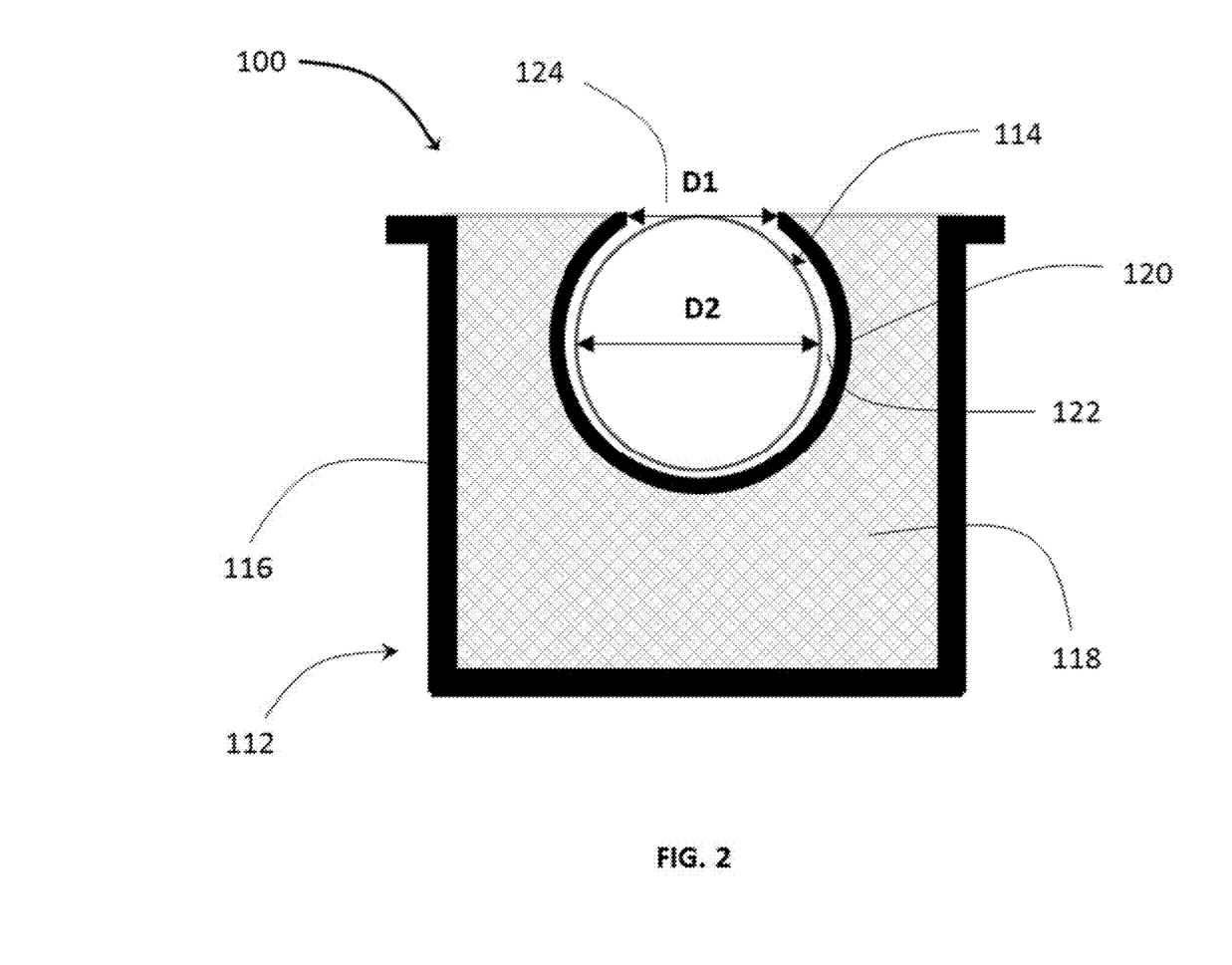
FIG. 2 is a cross-sectional side view of a representation of the packaging system in FIG. 1 at a position along line A-A.

Referring now to FIG. 2, cavity 122 of inner layer 120 of packaging system 100 includes opening 124 defined by first dimension D1. Inner layer 120, which in this example is spherical in shape, separates intermediate porous layer 118 from cavity 122. Article 114 is defined by second dimension D2, which is larger than first dimension D1. In the example shown, dimensions D1 and D2 define dimensions of diameters of the respective opening 124 and article 114. As best seen in FIG. 2, except at opening 124, inner layer 120 completely encloses article 114 when article 114 is placed in cavity 122. Consequently, inner layer 120 provides full surface support and insulation for article 114. Due to the elasticity of inner layer 120, opening 124 flexes and expands such that article 114 may be pushed through opening 124 into cavity 122 as shown in FIG. 2. In this manner, article 114 may be securely retained in cavity 122 and prevented from be ejected due to gravity or other forces experienced by packaging unit 112 during shipping. Article 114 may be removed from cavity 122 by manual extraction when required.

Exterior layer 116 and intermediate porous layer 118 provide external puncture protection and internal impact resistance, respectively, for article 114. The hardness of exterior layer 116 may be controlled by altering the density of this layer. For example, if an additive manufacturing process such as 3D printing is used to create packaging system 100, a dense exterior layer 116 may be printed to provide a relatively solid external barrier. The porosity of porous layer 118 may be adjusted such that the porous layer acts as a resilient member to provide a sufficient level of shock absorption and thermal insulation for article 114. Porous layer 118 may be, but is not limited to being, in the form of a honeycomb structure, a lattice structure, a truss structure, a bubble structure and a unit cell structure as disclosed in U.S. Patent Publication No. 2015/0258735, U.S. Pat. Nos. 8,728,387 and 9,180,010, the disclosures of all of which are hereby incorporated by reference herein as it is fully set forth herein. Inner layer 120 may be substantially solid, i.e., substantially non-porous, and substantially elastic.

Figure 3:
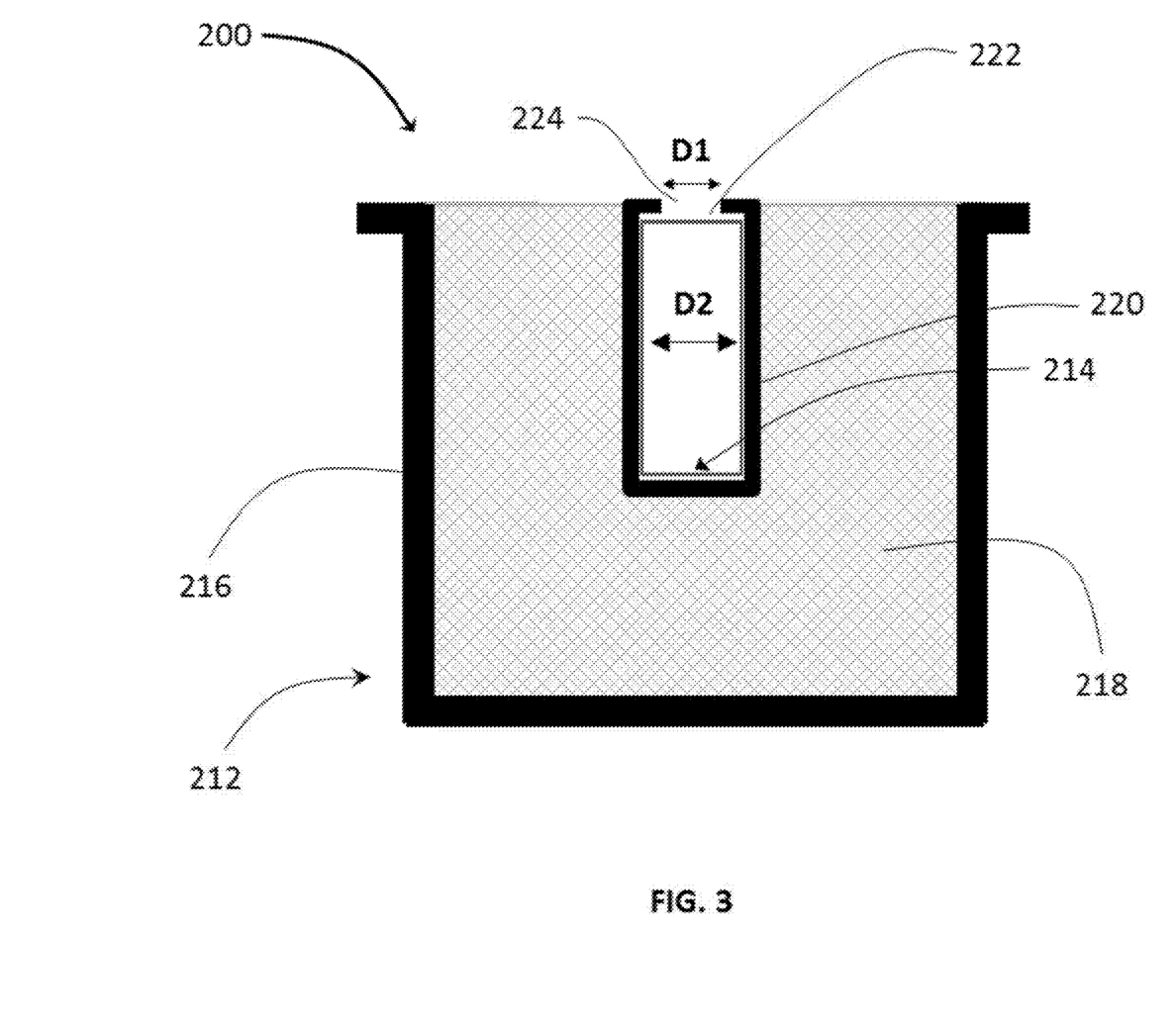
FIG. 3 is a cross-sectional side view of a packaging system in accordance with another embodiment.

As shown in FIG. 3, packaging system 200 is substantially the same as packaging system 100 with the notable exception that cavity 224 and article 214 are rectangularly shaped in this embodiment. Like elements for packaging system 200 are referenced with similar reference numerals within the 200-series. In this example, first dimension D1 defining opening 224 of cavity 222 is smaller than second dimension D2 of rectangularly shaped article 214. Inner layer 220 may be elastically deformed by pushing article 214 through opening 224 to secure the article within cavity 222. While circular and rectangular articles and corresponding inner layers of packaging units are illustrated in packaging systems 100 and 200, respectively, articles and corresponding inner layers of packaging units with other shapes may be used so long as the article is retained and protected by the packaging unit.

Figure 4:
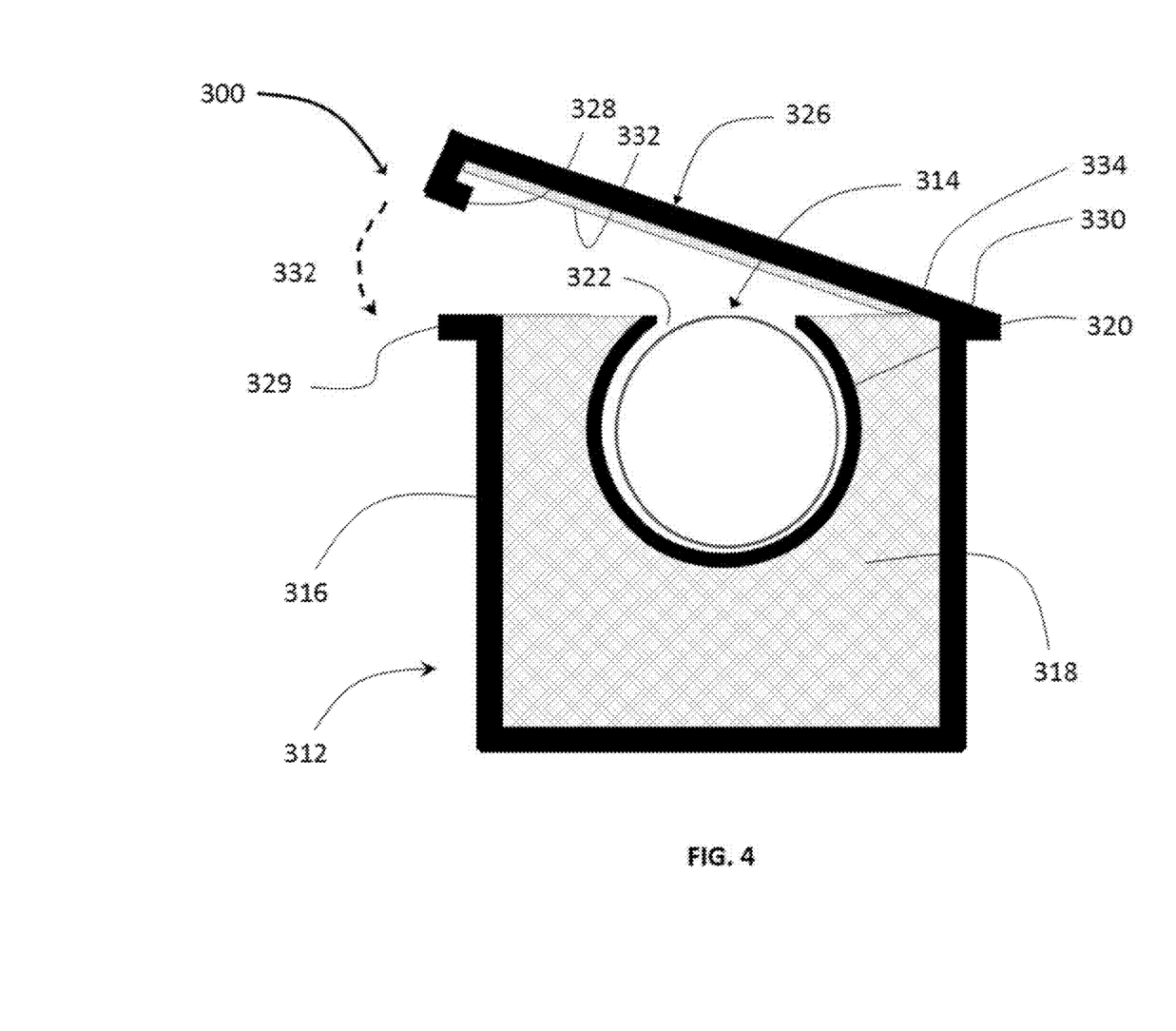
FIG. 4 is a cross-sectional side view of a packaging system in accordance with another embodiment.

As shown in FIG. 4, packaging system 300, which is also substantially similar to packaging system 100 with the notable exception that packaging system 300 includes self-locking lid 326. Like elements for packaging system 300 are referenced with similar reference numerals within the 300-series. Lid 326 includes hinged end 330 and locking end 328 on an end opposite the hinged end. After article 314 is secured in cavity 322, lid 326 may be locked in place by overlapping locked end 328 and rim 329 of packaging unit 312 which extends around an upper edge of exterior layer 316. In alternative arrangements, the locking end may include undercuts, snap-fit elements, grooves, slots, etc., to interface with corresponding features of the rim of the packaging unit. As shown in this example, packaging unit 312 completely covers and insulates article 314 when lid 326 is placed over cavity 322 and is secured to rim 329. As further shown, lid 326 may include solid exterior layer 334 over the exposed surfaces of the lid, inner layer 332 over the surface of the lid that contacts and interfaces with inner layer 320, and, in some arrangements, an intermediate porous layer (not shown) between the exterior layer and the inner layer. Exterior layer 334 may be made of the same material and have the same flexibility as exterior layers 116, 216, 316, the intermediate porous layer may be made of the same material as intermediate porous layer 118, 218, 318, and inner layer 332 may be made of the same material as inner layer 320. As in this example, lid 326 may be made of the same material, although in other arrangements, the various layers may be made of different materials than the other layers.

Packaging units, such as packaging units 112, 212, 312, may be fabricated using additive manufacturing techniques, such as but not limited to stereolithography (SLA), fused deposition modeling (FDM), continuous liquid interface production (CLIP), selective laser sintering (SLS), selective laser melting (SLM), electron beam melting (EBM), and other 3D printing technologies known to those of skill in the art. Medical-grade TPU and similar materials that provide a sterile packaging unit requiring no additional sterile barriers are available for use for the safe storage shipping and handling of articles such as medical devices as stand-alone materials.

Figure 5A:
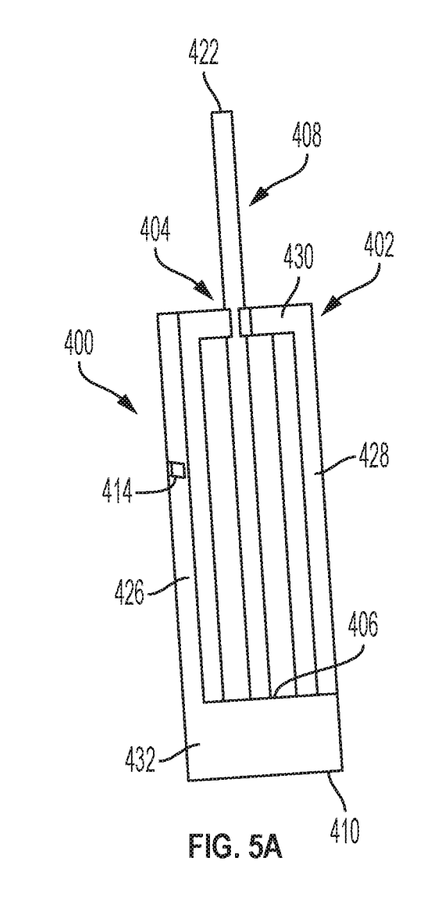
FIGS. 5A and 5B are perspective views of a tensioning device in accordance with another embodiment.
Figure 5B:
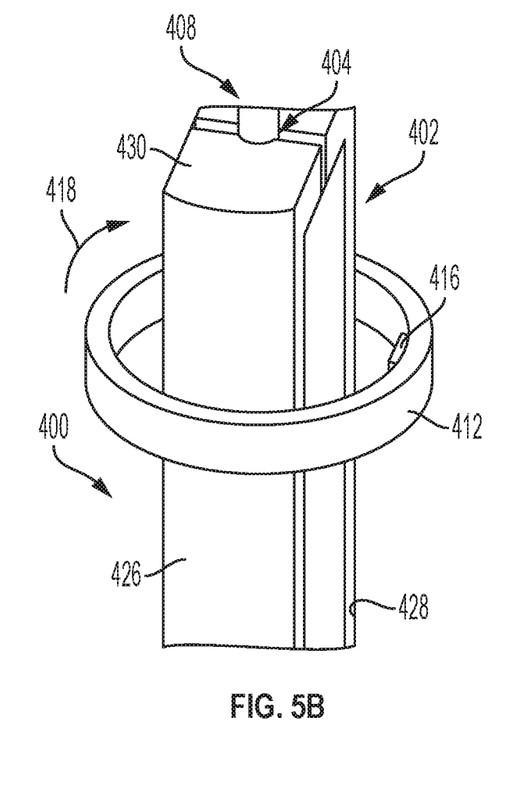

Referring now to FIGS. 5A and 5B, tensioning device 400 is a system for adjusting the tension of highly elastic filaments, such as medical-grade TPU, used with a 3D printing machine, e.g., the MakerBot Replicator® 2×. Tensioning device 400 includes frame 402 having two parallel arms 426, 428 each attached at one end to respective flanges 430, 432 that extend toward each other to define inlet port 404 and attached at their other ends to base 410 defining outlet port 406. As shown, feed filament 408 is received through both inlet port 404 and outlet port 406. Feed filament segment 422 of feed filament 408 may be connected to a feed spool (not shown), such as that used in the MakerBot Replicator® 2×, or any other filament feeding elements. Base 410 of frame 402 may be attached to printing head portion 424, as shown in FIG. 6, of a 3D printer (not shown).

Figure 6:
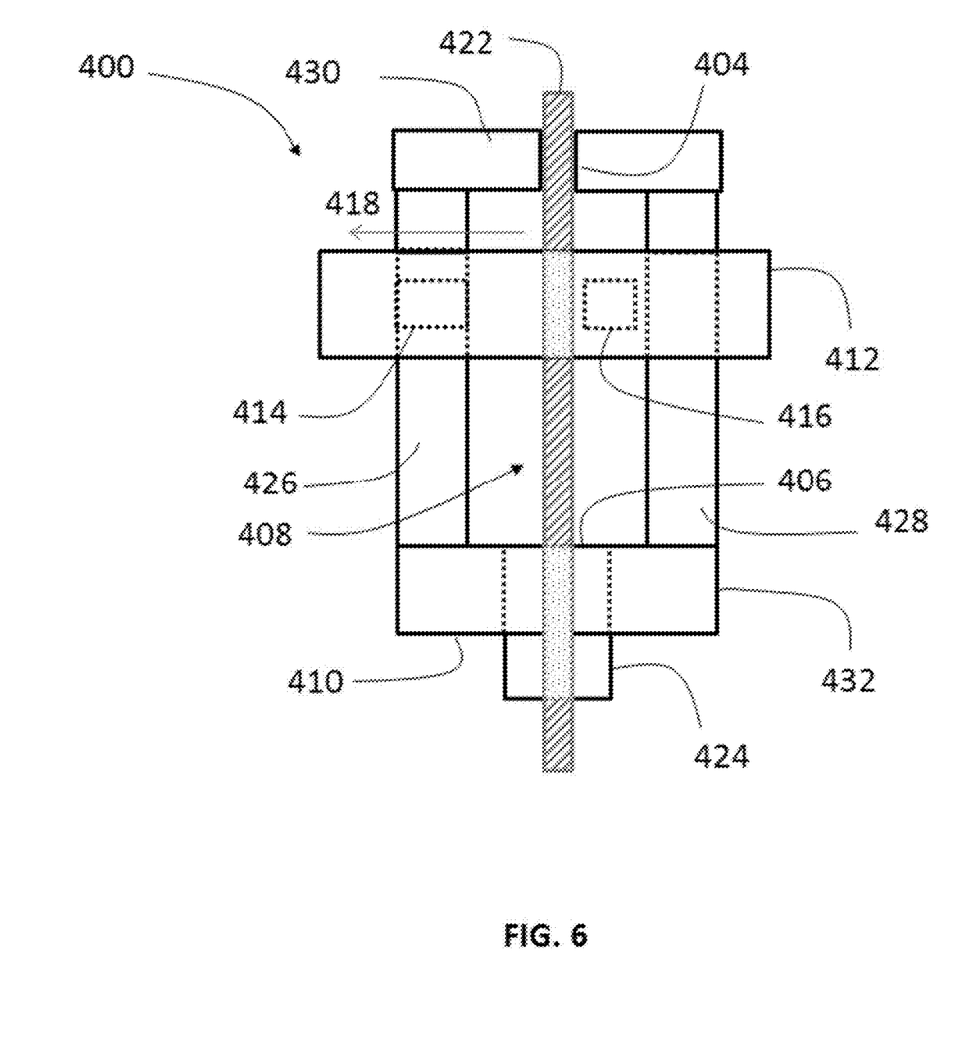
FIG. 6 is a cross-sectional side view of the tensioning device of FIGS. 5A and 5B.

As further shown in FIGS. 5A, 5B and 6, tensioning device 400 includes band 412 around frame 402. Band 412 includes projection 416 configured to engage with corresponding groove 414 on frame 402. Rotating band 412 in a first direction as indicated by directional arrow 418 will progressively engage projection 416 with groove 414, which will lead to narrowing of inlet port 404. In this example, band 412 is configured to apply a discrete amount of tension as best shown in FIG. 5B. As inlet port 404 is narrowed, it progressively contacts filament 422 thereby applying a compressive force between inlet port 404 and filament 422 which in turn creates tension in feed filament 408 between inlet port 404 and print head 424. In this manner, rotating band 412 alters the tension on feed filament 408 between inlet port 404 and printing head portion 424 and thereby allows for tension adjustment of feed filament 408 as it enters the printing head. Other configuration and processes to apply a discrete or a progressive amount of tension to the filament may also be used.

Figure 7:
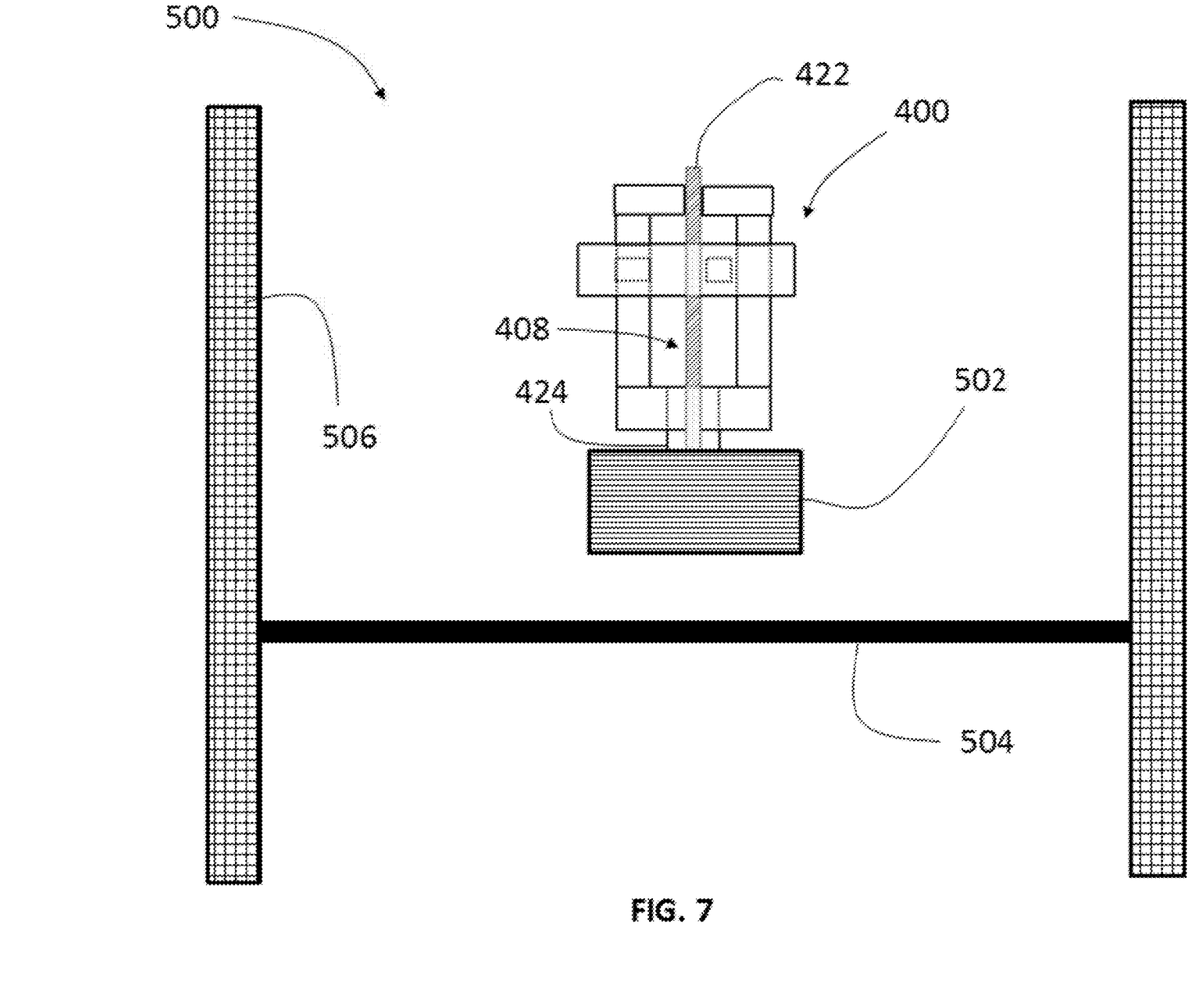
FIG. 7 is a side view of a 3D printing assembly, including the tensioning device of FIGS. 5A and 5B, in accordance with another embodiment.

As shown in FIG. 7, 3D printing assembly 500 includes a 3D printing machine and tensioning device 400. Feed filament 408 from a supply element such as a feed spool (not shown) is attached to tensioning device 400. The feed filament may be formed by converting a resin of the filament material, such as medical-grade TPU, into a molten state and then extruding the molten material into the feed filament. Base 410 of tensioning device 400 is mounted on a head portion 424 of printing head 502 of a 3D printing machine. The 3D printing machine includes frame 506 and build platform 504. Feed filament tension may be further adjusted depending on the feed filament material being used by rotating band 412 on tensioning device 400. In this manner, proper feed filament tension entering the printing head is maintained during printing to avoid jamming gears in the printing head. While a 3D printing assembly with tensioning device 400 is shown, other additive manufacturing techniques may also utilize the tensioning device.

Figure 8:
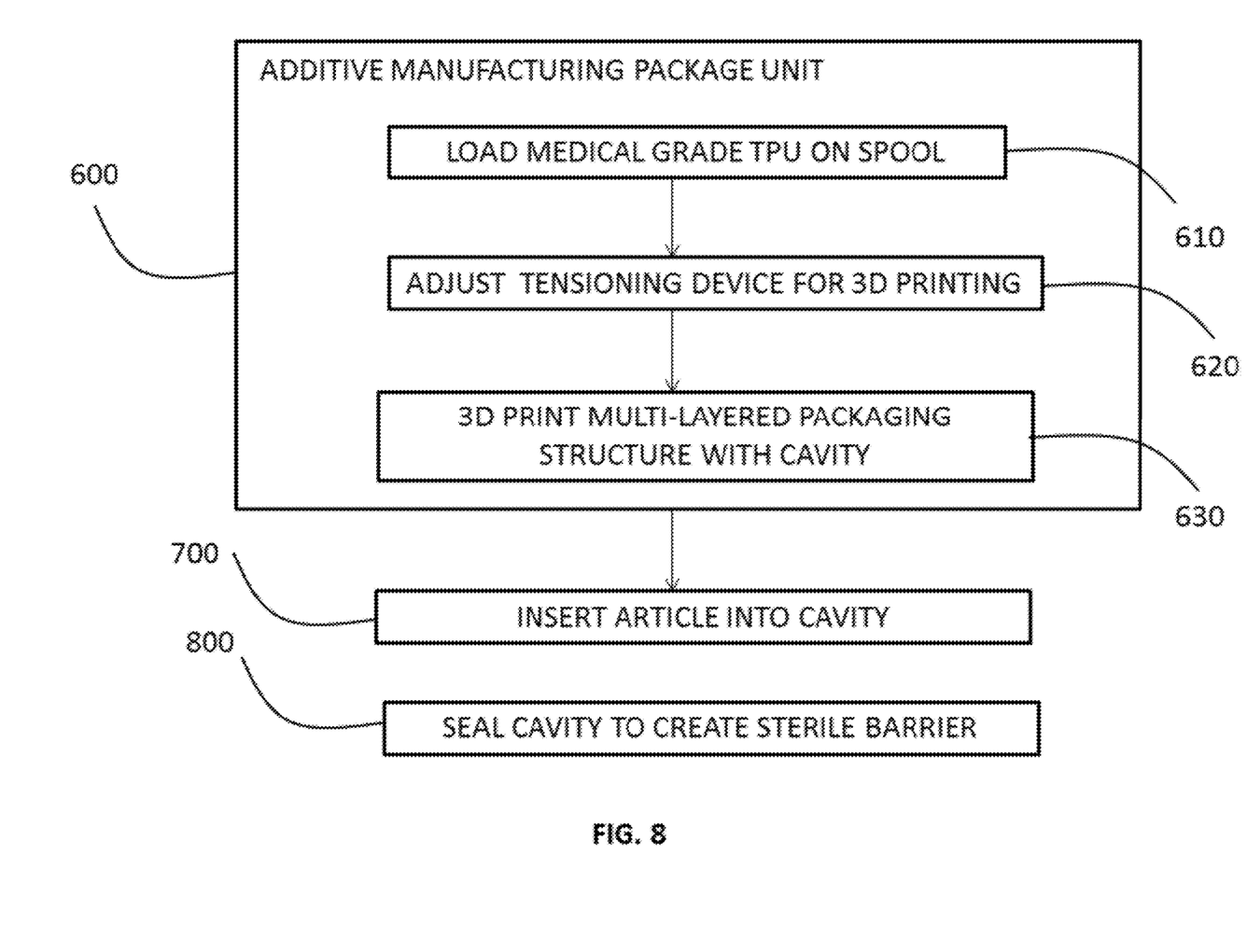
FIG. 8 is a process flow diagram of a process for packaging an article in accordance with an embodiment.

As shown in FIG. 8, via process 600, a monolithic multi-layered and multi-functional packaging unit with a cavity as disclosed herein is fabricated by 3D printing. In step 610, suitable feed filament material, e.g., elastomeric material that provides rigidity, shock absorption and sterile protection, such as medical-grade TPU, is loaded on a feed element such as a feed spool of a 3D printing assembly, such as but not limited to 3D printing assembly 500. In step 620, based on the material selection and the 3D printer requirements, a tensioning device, such as but not limited to tensioning device 400, located between the feed element and the printing head is suitably calibrated for the proper feed filament tension at the printing head. In step 630, the 3D printer with the calibrated tensioning device is used to generate the multi-layered packaging unit, such as but not limited to packaging units 112, 212, 312, having a cavity with an opening defining a first dimension. In step 700, an article, such as articles 114, 214, 314, defining a second dimension which is less than the first dimension is inserted through the opening and into the cavity such that the article is firmly secured within the packaging unit. In step 800, the cavity is sealed by placing a lid over the cavity and heating or utilizing a chemical polymerization process known to those skilled in the art thereby creating a sterile barrier to protect the packaged article. Alternative arrangements of this process may include additional steps of forming a packaging unit with a self-locking lid, and closing this lid after inserting the article to fully enclose the article on all sides While the present disclosure generally discusses articles which are medical devices, other articles may also be retained and protected by packaging units similar to those described in the present disclosure.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the paragraphs below.

The invention claimed is:

1. A packaging system comprising:
 a packaging unit comprising:
  a substantially solid first layer defining an exterior of the packaging system;
  a porous second layer;
  a plastic third layer defining a cavity with an opening having a first dimension, the first dimension being measured along a line extending across the opening, wherein the second layer is disposed between the first and third layers, the cavity having a third dimension greater than the first dimension, the third dimension being measured parallel to the line; and
 an article having a second dimension and being receivable in and removable from the cavity, the second dimension being substantially the same or greater than the first dimension such that the article is secured in the cavity when the article is received in the cavity;
 wherein the packaging unit is a monolithic structure.

2. The packaging system of claim 1, wherein the article is a medical implant.

3. The packaging unit of claim 1, wherein the first dimension is a diameter of the opening and the third dimension is a diameter of the cavity.

4. The packaging unit of claim 1, wherein when the opening has the first dimension, the article is at least partially enclosed.

5. A packaging unit comprising:
 a substantially solid first layer defining an exterior of the packaging unit;
 a porous second layer;
 a plastic third layer defining a cavity with an opening;
 wherein the second layer is disposed between the first and the third layers, the plastic third layer being flexible such that the opening is flexible between a first and a second dimension, the first and second dimension being measured along a line extending across the opening, the second dimension being greater than the first dimension, the cavity having a third dimension greater than the first dimension, the third dimension being measured parallel to the line; and
 wherein the packaging unit is a monolithic structure.

6. The packaging unit of claim 5, further comprising a cover that encloses the opening in a first position and exposes the opening in a second position.

7. The packaging unit of claim 6, wherein the cover encloses the cavity in the first position.

8. The packaging unit of claim 6, wherein the cover is hingedly attached to the first layer.

9. The packaging unit of claim 8, wherein the cover is inseparable from the first layer without fracturing at least one of the first layer and the cover.

10. The packaging unit of claim 5, wherein the first dimension is a diameter of the opening and the third dimension is a diameter of the cavity.

* * * * *